(12) United States Patent
Robert et al.

(10) Patent No.: US 7,887,686 B2
(45) Date of Patent: Feb. 15, 2011

(54) METHOD FOR ANALYZING HAEMOGLOBIN BY CAPILLARY ELECTROPHORESIS, A KIT FOR CAPILLARY ELECTROPHORESIS, AND USE OF A FLOW INHIBITOR IN SAID METHOD

(75) Inventors: Frédéric Robert, Mennecy (FR); Denis Simonin, Evry (FR); Jean-Baptiste Clement, Etiolles (FR)

(73) Assignee: SEBIA (FR)

( * ) Notice: Subject to any disclaimer, the term of this patent is extended or adjusted under 35 U.S.C. 154(b) by 866 days.

(21) Appl. No.: 11/280,025

(22) Filed: Nov. 16, 2005

(65) Prior Publication Data

US 2006/0102478 A1 May 18, 2006

(30) Foreign Application Priority Data

Nov. 18, 2004 (FR) .................................. 04 12263

(51) Int. Cl.
*G01N 27/447* (2006.01)
(52) U.S. Cl. .................. 204/451; 204/468; 204/601
(58) Field of Classification Search ......... 204/450–468, 204/600–616, 400, 403.01–403.15
See application file for complete search history.

(56) References Cited

U.S. PATENT DOCUMENTS

| | | | |
|---|---|---|---|
| 5,202,006 A * | 4/1993 | Chen | ........................... 204/451 |
| 5,439,825 A | 8/1995 | Chen | |
| 5,447,612 A | 9/1995 | Bier et al. | |
| 5,536,382 A * | 7/1996 | Sunzeri | ........................ 204/451 |
| 5,599,433 A * | 2/1997 | Keo et al. | ..................... 204/451 |
| 5,753,094 A * | 5/1998 | Alter et al. | ................... 204/451 |
| 6,083,372 A * | 7/2000 | Grover et al. | ................ 204/451 |
| 6,766,817 B2 | 7/2004 | da Silva et al. | |
| 2002/0162744 A1 * | 11/2002 | Nouadje et al. | ............. 204/451 |

FOREIGN PATENT DOCUMENTS

| | | |
|---|---|---|
| FR | 1.554.045 A | 1/1969 |
| WO | WO-97/04308 A1 | 2/1997 |

OTHER PUBLICATIONS

Daria Love, The Utilization of Zwitterionic Buffer System in the Plaque Assay of a Feline Calicivirus, 1973, AJEBAK 51 (Pt. 2), 263-266.*

(Continued)

*Primary Examiner*—Alexa D Neckel
*Assistant Examiner*—Jennnifer Dieterle
(74) *Attorney, Agent, or Firm*—Lerner, David, Littenberg, Krumholz & Mentlik, LLP (57) ABSTRACT

The invention concerns a method for free solution capillary electrophoresis at an alkaline pH to analyze samples comprising haemoglobin, in which the sample is passed through a capillary containing an analysis buffer, comprising at least one step in which the sample is introduced into a capillary tube containing a solution of analysis buffer, characterized in that the buffer is of the zwitterionic type and in that it is associated with at least one flow inhibitor. It also concerns the use of CE flow inhibitors associated with at least one zwitterionic buffer, and a kit for analyzing haemoglobin by capillary electrophoresis.

24 Claims, 13 Drawing Sheets

OTHER PUBLICATIONS

Roy et al., Buffer Standards for the Physiological pH of the Zwitterionic Compound, TAPS, From5 to 55° C, Journal of Solution Chemistry, vol. 35, No. 4, Apr. 2006, p. 552 (see chemical strucutre).*

Mohammad et al. (Clinical Application of Capillary Isoelectric Focusing on Fused Silica Capillary for Determination of Hemoglobin Variants, Clinical Chemistry 1997, 43: 1798-1799).*

Camilleri (Capillary Electrophoresis, 1997, pp. 370-371).*

Hempe et al. (Capillary isoelectric focusing of hernoglobin variants in the pediatric clinical laboratory, Elecrrophoresis 1997, 18, 1785-1795).*

Ishioka et al., "Detection of Abnormal Haemoglobin by Capillary Electrophoresis and Structural Identification", Biomedical Chromatography, vol. 1, pp. 224-226, 1992.

Sahin et al., "Haemoglobin analysis by capillary zone electrophoresis", Journal of Chromatography A, vol. 709, pp. 121-125, 1995.

Jenkins et al., "Capillary electrophoresis as a clinical tool" Journal of Chromatography B, vol. 682, pp. 23-34, 1996.

Jenkins et al., "Evaluation of hemoglobin $A_2$ quantitation assay and hemoglobin variant screening by capillary electrophoresis", J.Cap. Elec. vol. 004, No. 3, pp. 137-143, 1997.

Jenkins et al., "Capillary isoelectric focusing of haemoglobin variants in the clinical laboratory", Clinica Chimica Acta, vol. 289, pp. 121-132, 1999.

Shihabi et al., "Hemoglobin $A_2$ quantification by capillary zone electrophoresis", Electrophoresis 2000, vol. 21, pp. 749-752, 1999.

Hempe et al., "Separation of hemoglobin variants with similar charge by capillary isoelectric focusing: Value of isoelectric point for identification of common and uncommon hemoglobin variants", Electrophoresis 2000, vol. 21, pp. 743-748.

* cited by examiner

FIG 1

|      | %    |
|------|------|
| HbA  | 44,0 |
| HbF  | 7,1  |
| HbS  | 46,5 |
| HbA2 | 2,4  |

FIG 2

|       | %    |
|-------|------|
| HbA   | 60,9 |
| HbF   | 1,6  |
| MetHb | 3,9  |
| HbA2  | 4,0  |
| HbC   | 29,6 |

FIG 3

|  | % |
|---|---|
| HbA | 65,2 |
| MetHb | 7,4 |
| HbE | 23,5 |
| HbA2 | 3,9 |

FIG 4

|  | % |
|---|---|
| HbA | 55,6 |
| HbF | 4,8 |
| HbD | 18,4 |
| HbS | 18,2 |
| HbA2 | 3,0 |

|  | % |
|---|---|
| HbA | 91,6 |
| HbF | 2,6 |
| MetHb | 1,9 |
| HbA2 | 3,9 |

FIG 6D

|      | %    |
|------|------|
| HbA  | 46,2 |
| HbF  | 3,3  |
| HbS  | 47,7 |
| HbA2 | 2,8  |

|      | %    |
|------|------|
| HbA  | 55,5 |
| HbF  | 3,1  |
| HbS  | 38,8 |
| HbA2 | 2,6  |

FIG 7D

METHOD FOR ANALYZING HAEMOGLOBIN BY CAPILLARY ELECTROPHORESIS, A KIT FOR CAPILLARY ELECTROPHORESIS, AND USE OF A FLOW INHIBITOR IN SAID METHOD

The present invention relates to a method for separating haemoglobin by capillary electrophoresis, to buffer compositions for use in said separation, and to kits for analyzing haemoglobin by capillary electrophoresis.

When analyzing haemoglobin $A_2$ and haemoglobin variants, in particular in biological liquids such as blood, for analytical and in particular for diagnostic purposes, and thereby to separate haemoglobins by electrophoresis, the use of capillary electrophoresis (CE) techniques is known. The term "haemoglobins" means any normal or abnormal haemoglobin and variants of said haemoglobins. One advantage of capillary electrophoresis resides in the fact that only very small quantities of biological liquids to be analyzed are necessary. Further, separation by that technique can be very rapid provided that high voltages can be used without heating the sample too much during separation.

The technique of choice is analysis by capillary isoelectrofocusing (CIEF). This method can produce a high resolution between the various forms of haemoglobin (Hempe) (7). However, it is difficult to automate and, because coated capillaries have to be used to prevent electro-osmotic flow, it is difficult to make it compatible with analyses carried out in series.

A further technique known as "dynamic double coating" may be carried out with commercial kits sold as the "Analis HbA$_2$-CE kit" or "CEofix HbA$_2$-CE kit" from Analis. That technique involves initial rinsing of the capillary with a solution containing a polycation at a pH of 4.7 followed by a second rinse with an analysis buffer containing a polyanion, at a pH of 8.7. In that "double coating" method, the quantity of negative charge present on the internal wall of the capillary is higher than on a naked capillary, and so the electro-osmotic flow is even greater. That dynamic double coating method cannot, however, separate HbA$_2$, HbC and HbE fractions sufficiently well, rendering quantitative analysis of the HbA$_2$ fraction impossible in the presence of HbC or HbE variants. Further, since HbS and HbD fractions have the same electrophoretic position, complementary analysis in an acidic medium is necessary to determine the type of variant present in the sample. Finally, the double coating has to be produced again between each sample analysis, rendering the method costly and difficult to employ for mass-produced tests.

Further, free solution haemoglobin separation has been described, but it does not satisfy the expected criteria for accuracy, resolution or rapidity to be able to rationalize CE haemoglobin analyses. Ishoka (1) (1992) described the separation of haemoglobins using a borate buffer (100 mM) at a pH of 9.98 with a migration time of the order of 50 minutes, i.e. incompatible with currently expected times for analyzing haemoglobins. The same type of buffer under similar pH and concentration conditions (Jenkins) (3), (4) and (5) can only produce insufficient resolutions between the HbA, HbF and HbS fractions. Sahin (2) describes more acidic pH conditions, but obtained deeply unimpressive results for resolution between the HbA, HbF, HbS and HbA$_2$ fractions with lower concentrations (20 mM) of borate or with barbital (50 mM) at a pH of 8.5, and also deeply unimpressive results for resolution between the HbA, HbS and HbA$_2$ fractions for Tris buffer (1 M) at a pH of 8.0. Further, Tris/arginine combinations (Shihabi) (6) have been used and even though they allowed HbA/HbS separation, HbC/HbE and HbA$_2$ fractions were not resolved. Finally, U.S. Pat. No. 5,202,006 and U.S. Pat. No. 5,439,825, which describe the use of barbital or ethylbarbital, could only produce low resolutions between the principal haemoglobins, namely HbA, HbF, HbS and HbC.

Thus, there exists a need for a method for analyzing haemoglobin and in particular haemoglobin $A_2$ which allows single step analysis without a double coating, which can be carried out automatically and in series, and which guarantees satisfactory resolution between the HbA$_2$, HbC, HbD, HbE, HbS, HbF and HbA forms in particular.

The Applicant has now demonstrated that by using a zwitterionic analysis buffer associated with a flow inhibitor, it is possible to obtain greatly improved separation of the fractions mentioned above, in a single step, thus avoiding complementary separations and without a double coating, which simplifies its implementation.

Thus, the present invention concerns separating haemoglobins in biological samples by capillary electrophoresis, in which method the biological sample comprising said haemoglobins is passed through a capillary containing an analysis buffer, comprising at least one step in which the sample is introduced into a capillary tube containing a solution of analysis buffer, and in which the buffer is of the zwitterionic type and is associated with at least one flow inhibitor. Said step is generally followed by separation of haemoglobins, migration and detection of the various variants.

The zwitterionic buffer used in the invention is a zwitterionic buffer buffering between pHs of 8 and 10, comprising at least one amine function and at least one acidic function and at least one hydroxyl function in the position opposite to the acidic function. The term "acidic function" as used here means the carboxylic acid function or the sulphonic acid function. Said zwitterionic buffer may be formed by one or two molecules: in the case in which the amine function is carried by a first molecule without an acidic function, said first molecule is associated with a second molecule carrying an acidic function, in particular a carboxylic or sulphonic acid function or an amino acid. An example of an amino acid which may be cited is glycine.

According to the invention, the flow inhibitors are of the aliphatic or cyclic diamine or polyamine type. They are selected from aliphatic diamines or polyamines and/or cyclic diamines or polyamines, for example. Aliphatic diamines or polyamines are preferred. Examples of aliphatic diamines which may be cited are 1,3-diaminopropane, 1,4-diaminobutane, 1,5-diaminopentane, 1,6-diaminohexane, N,N'-dimethyl-1,6-hexanediamine, N,N,N',N'-tetramethyl-1,4-butanediamine and their acceptable derivatives and salts. Examples of aliphatic polyamines which may be cited are diethylenetriamine, spermine, tetraethylenepentamine and their acceptable derivatives and salts. The flow inhibitors may be used as a mixture.

Acceptable salts which may be cited are the hydrochloride salts or the like. Examples of derivatives which may be cited are derivatives of the above compounds wherein one or more carbon atoms of the aliphatic chain is/are substituted with one or more alkyl groups and/or one of the hydrogen(s) of the free amines is/are substituted with one or more alkyl groups.

The analysis buffer solution may also comprise other additives, in particular other additives intended to improve the separation of the various haemoglobins.

Further, the invention concerns the use of compounds known for their electrophoretic flow inhibiting activity in free solution CE in association with at least one zwitterionic buffer.

As will become apparent from the following examples, using the associations of the invention can greatly improve the resolution of haemoglobin and haemoglobin variants. It can thus improve the accuracy and precision of qualitative and quantitative analysis of the variants compared with analyses carried out using known methods. It can also allow $HbA_2$ to be quantified even in the presence of HbC or HbE.

The zwitterionic buffer—flow inhibitor associations of the invention are of particular use in analyzing samples in which normal or variant haemoglobins of the $HbA_2$, HbC, HbD, HbE, HbS, HbF and/or HbA type are present, to detect and/or quantify them.

Finally, the invention pertains to kits for analyzing haemoglobin $A_2$ and haemoglobin variants in a biological sample by CE, comprising at least one analysis buffer solution containing at least one zwitterionic type analysis buffer or a zwitterionic buffer and at least one flow inhibitor, and an optional pH modifier. Thus, the kits may comprise at least one analysis buffer and a flow inhibitor according to the invention, and one or more solution(s) for rinsing capillaries and/or dilution segments and/or one (or more) diluent(s) for the sample to be analyzed. They may also comprise at least one haemolysing solution. In said kit, the buffer and the inhibitor(s) and diluent (s) or other additives may be stored separately for mixing extemporaneously, or stored as a mixture. This kit also optionally comprises instructions for carrying out the analysis and/or software support information.

Other advantages and characteristics of the invention will become apparent from the following description of examples made with reference to the accompanying drawings.

FIG. 2=HbF and HbS; FIG. 3=HbC; FIG. 4=HbE; FIG. 5=HbS and HbD-Los Angeles;

The conditions for carrying out capillary electrophoresis are known in the art. They usually include rinsing the capillaries with a rinsing solution, rinsing with the analysis buffer solution, optionally diluting the sample once or more, injection of the sample, migration and detection. Said steps may be carried out using automated machines.

Sample conditions for carrying out capillary electrophoresis are conditions suitable for using the automated Capillarys apparatus (SEBIA).

Examples of zwitterionic buffers for use in the invention which may be cited are "Tris" type buffers having several hydroxyl groups, specific examples of which are the following buffers: Tris (2-amino-2-[hydroxymethyl]-1,3-propanediol), tricine (N-tris[hydroxymethyl]methylglycine), TAPS (N-tris[hydroxymethyl]methyl-3-aminopropanesulphonic acid), TABS (N-tris[hydroxymethyl]methyl-4-aminobutanesulphonic acid), or AMPD (2-amino-2-methyl-1,3-propanediol) or bis Tris propane (1,3-bis[tris (hydroxymethyl)methylamino]propane), the last two and Tris possibly being associated with an amino acid.

Other molecules having a smaller number of hydroxyl groups may also be suitable, such as AMPSO (3-[(1,1-dimethyl-2-hydroxymethyl)amino]-2-hydroxy-propanesulphonic acid), bicine (N,N-bis[2-hydroxyethyl]glycine), HEPBS (N-[2-hydroxyethyl]piperazine-N'-[4-butanesulphonic] acid), in particular.

A preferred zwitterionic buffer from those cited above is tricine.

These buffers are known and commercially available. They may also be used as a mixture.

Preferred flow inhibitors from those cited above are 1,4-diaminobutane (DAB), 1,5-diaminopentane, 1,6-diaminohexane, diethylenetriamine (DETA) and N,N,N',N'-tetramethyl-1,4-butanediamine. The inhibitors may also be used as a mixture.

1,4-diaminobutane hydrochloride is preferably associated with the tricine.

The term "sample of the invention" means the biological sample to be analyzed, i.e. any biological liquid comprising red corpuscles from healthy or sick patients. The human biological liquids may be blood, which may be normal or abnormal, washed, decanted, centrifuged or whole. Further, the blood may be haemolyzed.

In addition to human biological samples, samples of animal origin may also be analyzed. The samples may also be of synthetic origin, and the method of the invention may then be aimed at monitoring production, for example.

The sample may be initially diluted with a suitable diluting solution, a haemolyzing solution or an analysis buffer solution, for example.

The CE methods employing zwitterionic buffer/flow inhibitor associations of the invention are of particular use in analyzing blood and separating haemoglobin and its variants in human samples.

According to the invention, the pH of the analysis buffer solution is in the range 8 to 11, preferably in the range 8 to 10.

The analysis buffer solutions of the invention may also comprise at least one pH modifier. Examples of pH modifiers which may be used are compounds selected from lithium hydroxide, sodium hydroxide, potassium hydroxide, rubidium hydroxide, caesium hydroxide, francium hydroxide, or a mono-, di-, tri- or tetra-alkyl ammonium hydroxide containing 1 to 8 carbon atoms in the alkyl portion.

According to the invention, the buffers are used in analysis buffer solutions under the usual conditions and concentrations, namely of the order of 20 to 500 mM, preferably 100 to 250 mM.

The flow inhibitors are used in the buffer solutions in concentrations in the range from about 0.01 to 50 mM, preferably in the range about 0.10 to 20 mM.

Further, the buffer solution may comprise one or more additives which may modify the ionic strength.

Examples of such compounds which may be cited are salts such as sulphates, chlorides, for example, and mixtures thereof.

The haemolyzing solution can carry out haemolysis of red corpuscles containing haemoglobin $A_2$ and haemoglobin variants. It is also used to dilute the sample before EC analysis. Depending on its composition, it may allow complete lysis of red corpuscles using a slight additional mechanical movement (vortex, agitation, ... )

The haemolyzing solution can carry out haemolysis of red corpuscles containing haemoglobin $A_2$ and haemoglobin variants. It is also used to dilute the sample before CE analysis. Depending on its composition, it may allow complete lysis of red corpuscles using a slight additional mechanical movement (vortex, agitation, ... )

The pH of the haemolysing solution is in the range 8 to 11, preferably in the range 8 to 10.

The buffer solutions of the invention are prepared in the usual manner for analysis buffer compositions, namely by adding the constituents in the liquid form or the solid form for dilution, to an acceptable support. The support is usually water, which may be distilled or demineralized.

The materials employed for the capillaries are those normally used in capillary electrophoresis. Fused silica capillaries may be used. Their internal diameter may be from 5 to 2000 μm. Preferably, capillaries with an internal diameter of 200 μm, preferably less than 100 μm, are used. Preferably, capillaries with an untreated internal surface are used. The skilled person will be able to adapt the nature of the capillary and its size to the requirements of the analysis.

The use of such naked capillaries constitutes an advantage of the invention.

The haemoglobins may be analyzed at a wavelength of about 200 nm, on haemolyzed blood obtained from washed, decanted or centrifuged blood. However, to avoid interference with plasma proteins, they are preferably analyzed at a wavelength of about 415 nm, using haemolyzed blood obtained from washed, decanted, centrifuged or whole blood.

EXAMPLES

Materials and Methods

A) Capillary Electrophoresis

Capillary electrophoresis of clinical samples was carried out on CE apparatus equipped with a fused silica capillary with an internal diameter of 25 microns.

Detection was carried out under optimized conditions, at about 415 nm.

The samples were placed in the Capillarys apparatus (SEBIA) and automatically injected by hydrodynamic injection. The samples were separated in less than 8 minutes by applying an electric field of about 550 V/cm. The capillary was rinsed before each analysis with 0.25 M sodium hydroxide then with a solution of analysis buffer.

Analysis buffers:

The chemical products used were analytical grade product.

The 200 mM tricine—15 mM 1,4-diaminobutane (A) buffer was prepared by dissolving 35.84 g of tricine in about 900 ml of demineralized water then by adding 2.32 g of 1,4-diaminobutane hydrochloride (DAB). The pH was adjusted to 9.37 at 22° C. with about 38.3 ml of 5M NaOH and the volume of the buffer solution was adjusted to 1 l with demineralized water.

The 200 mM tricine—15 mM 1,5-diaminopentane (B) buffer was prepared by dissolving 35.84 g of tricine in about 900 ml of demineralized water then by adding 2.62 g of 1,5-diaminopentane hydrochloride. The pH was adjusted to 9.40 at 22° C. with about 38.4 ml of 5M NaOH and the volume of the buffer solution was adjusted to 1 l with demineralized water.

The 200 mM tricine—20 mM diethylenetriamine (C) buffer was prepared by dissolving 35.84 g of tricine in about 900 ml of demineralized water then by adding 2.06 g of diethylenetriamine (DETA). The pH was adjusted to 9.40 at 22° C. with about 32.4 ml of 5M NaOH and the volume of the buffer solution was adjusted to 1 l with demineralized water.

The 200 mM tricine—8 mM N,N,N',N'-tetramethyl-1,4-butanediamine (D) buffer was prepared by dissolving 35.84 g of tricine in about 900 ml of demineralized water then by adding 1.15 g of N,N,N',N'-tetramethyl-1,4-butanediamine. The pH was adjusted to 9.19 at 22° C. with about 34.7 ml of 5M NaOH and the volume of the buffer solution was adjusted to 1 l with demineralized water.

B) Clinical Samples

For CE, human blood, decanted or centrifuged, was diluted to $1/6^{th}$ in the haemolyzing solution. This was prepared by dissolving 1.00 g of Triton X100, 2.50 g of saponine, 3.63 g of Tris in about 900 ml of demineralized water. The pH was adjusted to 8.70 at 22.0° C. and the volume of the solution was adjusted to 1 l with demineralized water. The chemical products employed were of analytical grade.

Examples 1 to 5

A solution of tricine/DAB.2HCl analysis buffer was prepared as described above.

Electrophoresis was carried out using the above method, on human blood.

Figure 1:
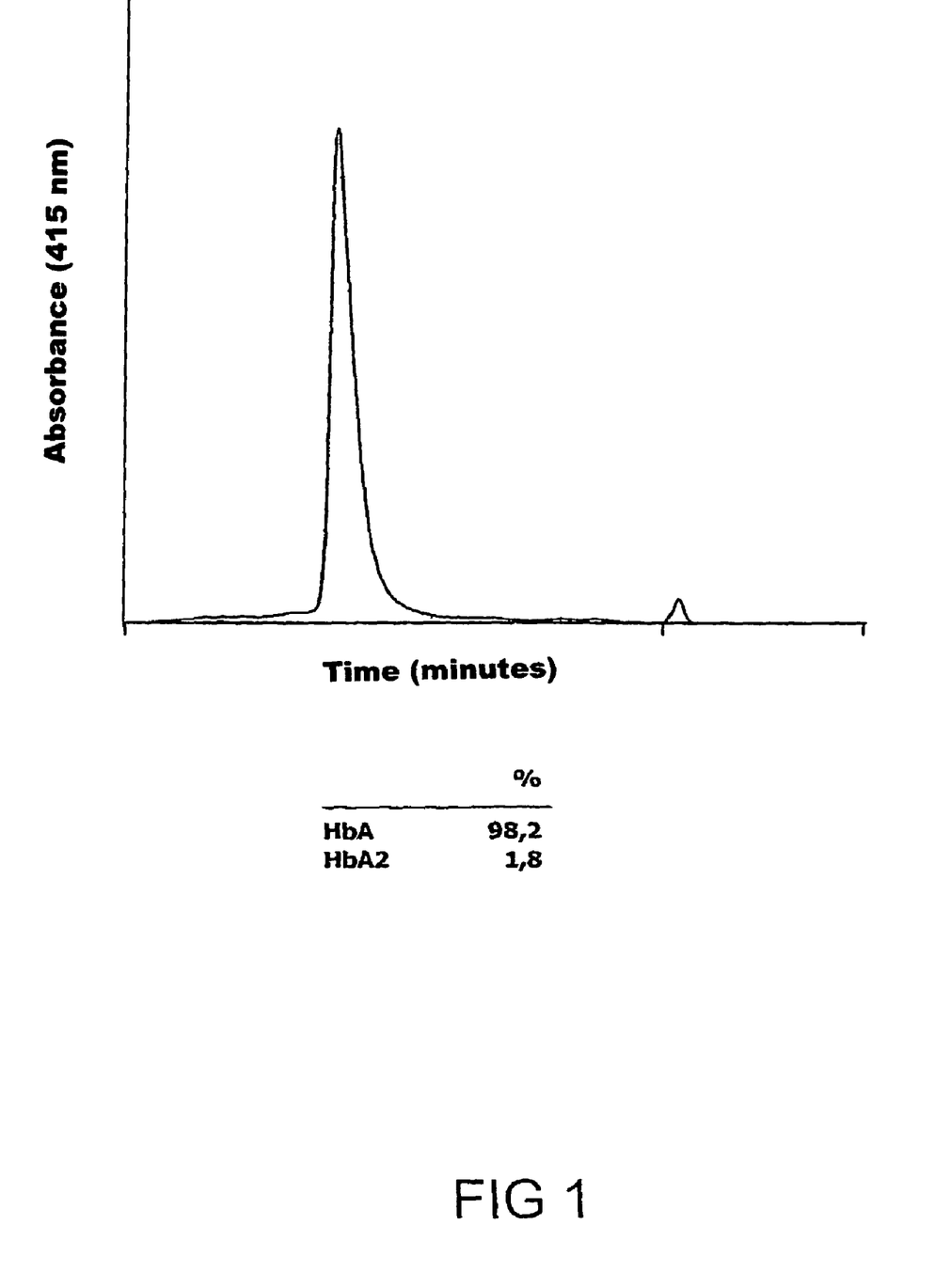
FIG. 1 shows an electrophoregram of normal human blood (HbA, $HbA_2$) analyzed by capillary electrophoresis using a buffer solution of the invention.

Example 1: analysis of normal human blood with HbA as the principal peak and $HbA_2$ as the smaller fraction (FIG. 1).

Figure 2:
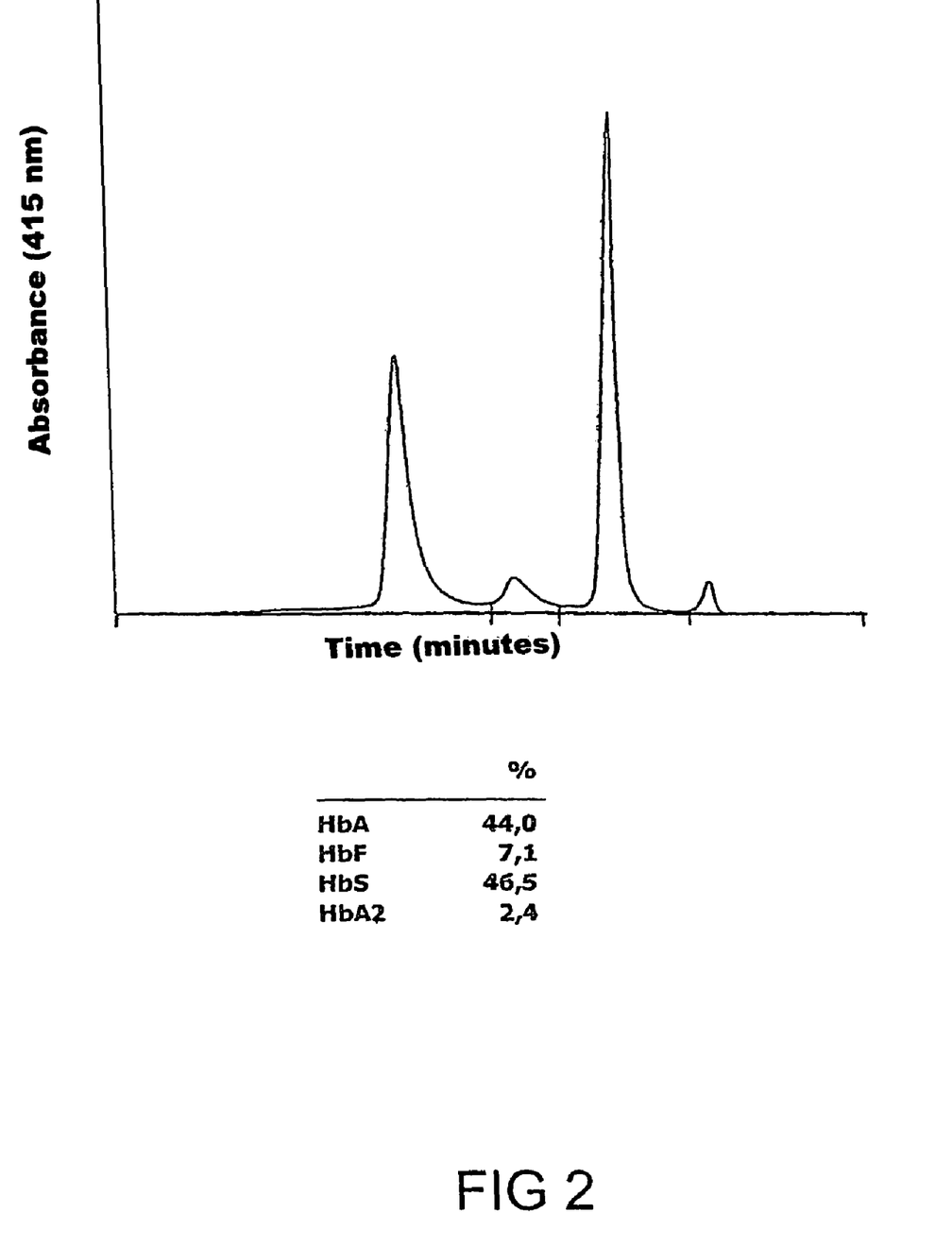
FIGS. 2 to 5 each show an electrophoretogram of blood analyzed by capillary electrophoresis using the same buffer solution. The blood respectively comprises the following variants.

Example 2: analysis of diseased human blood, which shows a smaller. HbA fraction, an augmented HbF fraction, a strong HbS fraction and a normal $HbA_2$ fraction. Heterozygous HbS was the origin of drepanocytosis (sickle cell anaemia) (FIG. 2).

Figure 3:
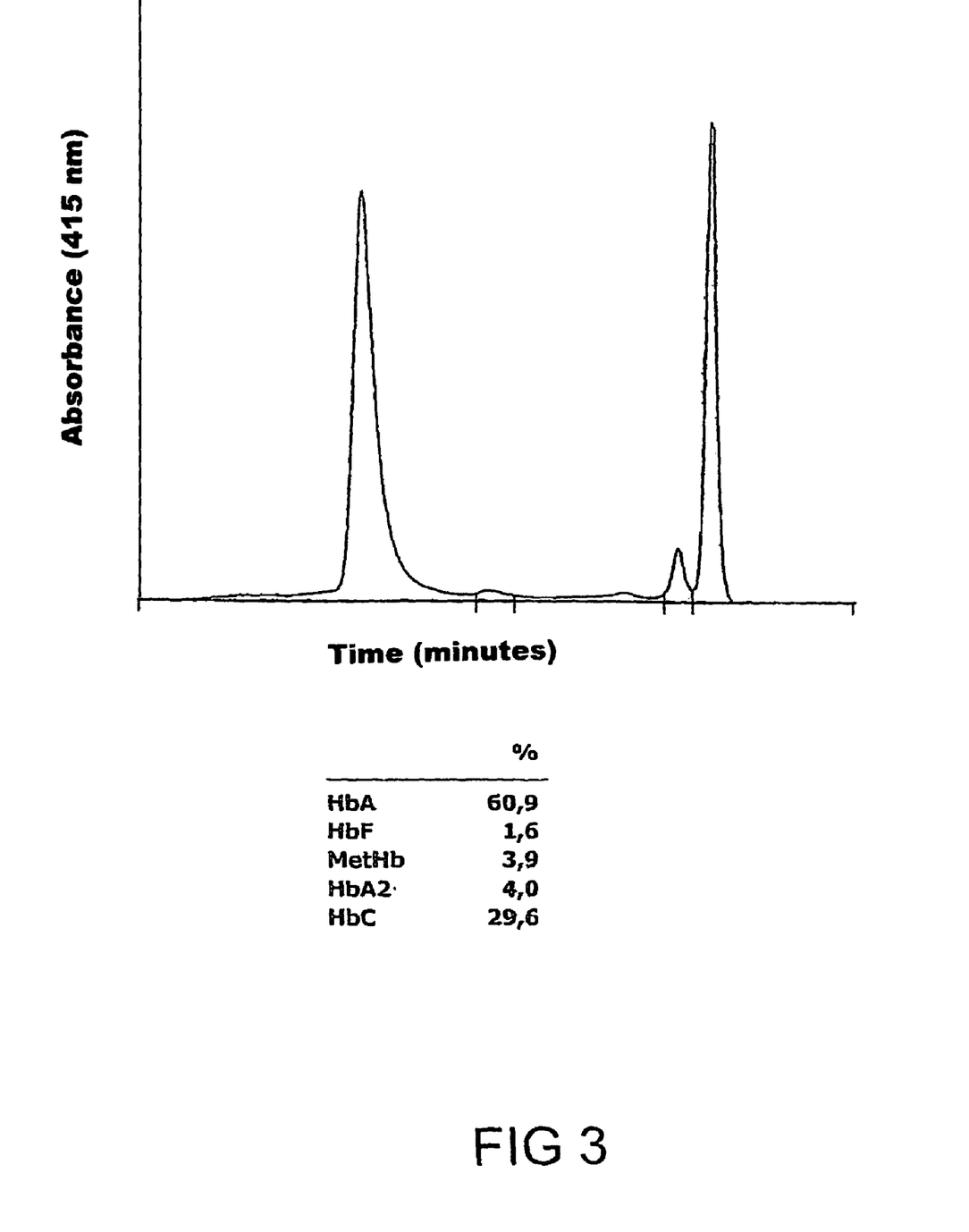

Example 3: analysis of diseased human blood presenting A/C heterozygosity. The HbC fraction leaves just before the $HbA_2$ fraction from which it is well resolved. This good resolution authorizes quantification of $A_2$ which means that the diagnosis could be orientated towards a case of β-thalassaemia, i.e. with an augmented $HbA_2$ fraction (FIG. 3).

Figure 4:
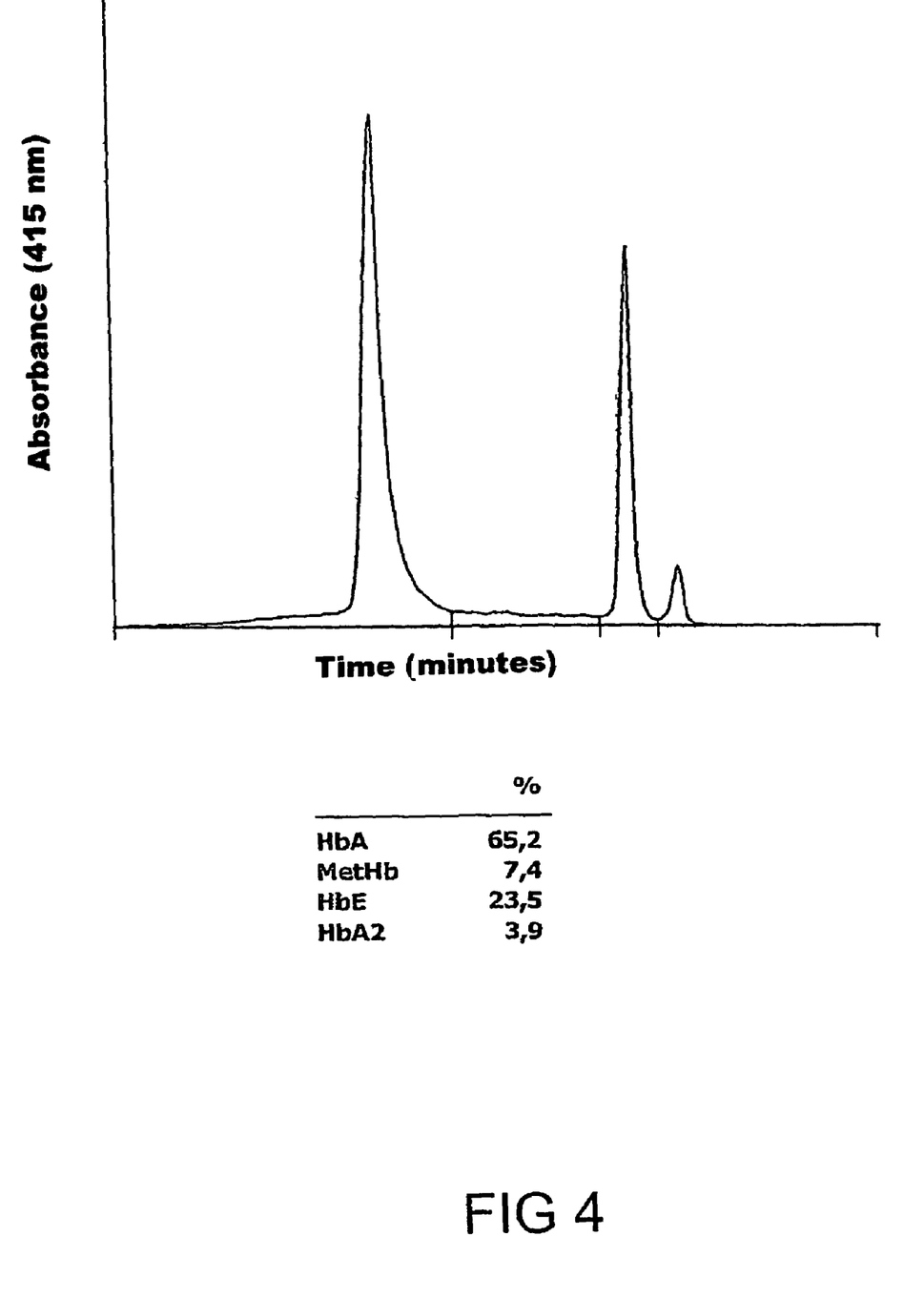

Example 4: analysis of human blood presenting A/E heterozygosity. The HbE fraction leaves just after the $HbA_2$ fraction from which it is completely resolved. Thus, there is no problem in quantifying $HbA_2$ in the presence of HbE (FIG. 4).

Figure 5:
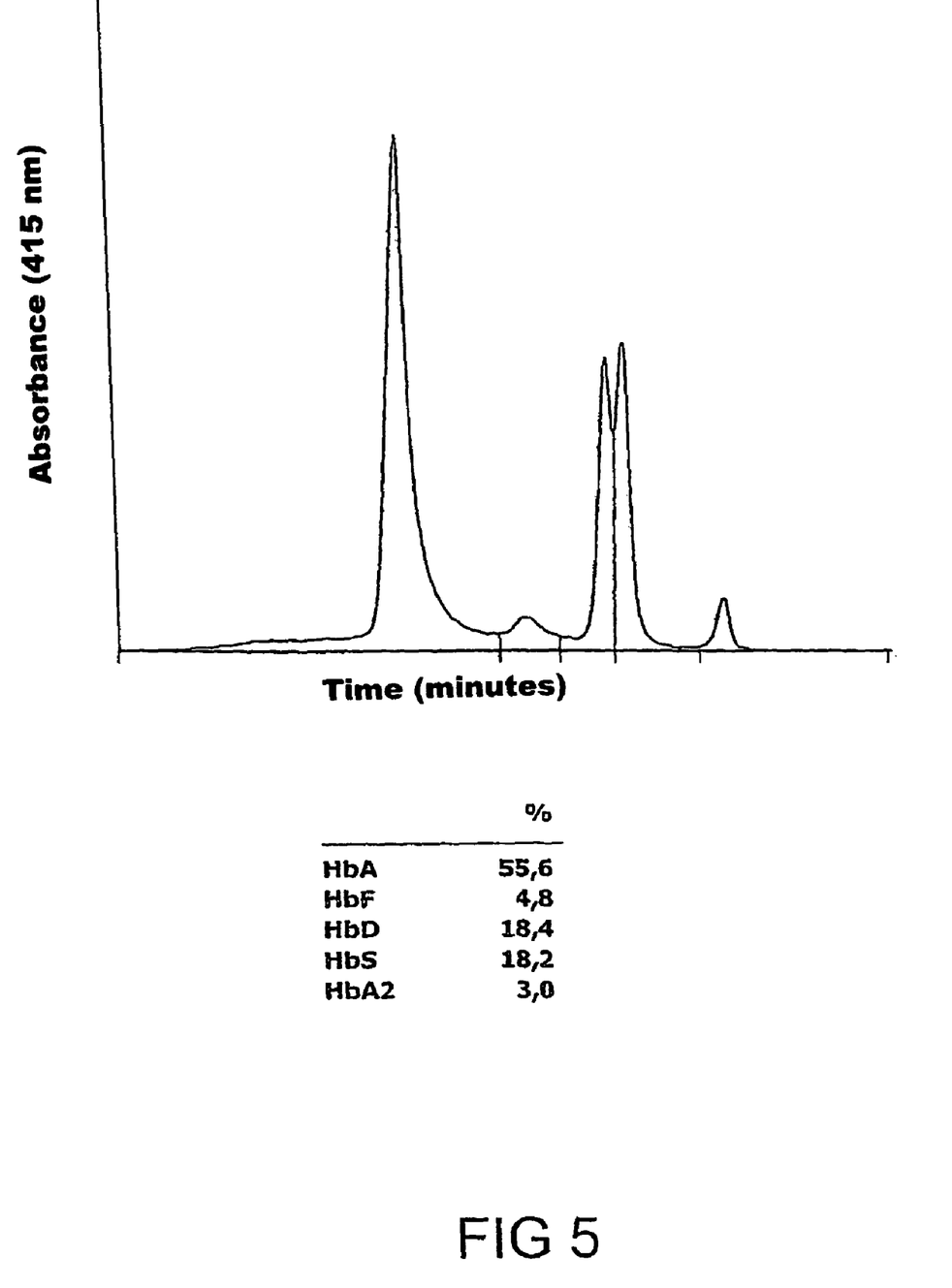

Example 5: Analysis of a mixture of blood presenting A/S heterozygosity and blood presenting A/D Los Angeles heterozygosity. The HbS and HbD fractions are partially resolved, which means that they can be distinguished from each other without the need for complementary analysis (FIG. 5).

Example 6: analysis of β-thalassaemic human blood, i.e. having an augmented percentage of $HbA_2$ function and having a small HbF fraction.

Four analysis buffer solutions A, B, C and D were prepared as above.

Electrophoresis was carried out using the method described above.

Figure 6A:
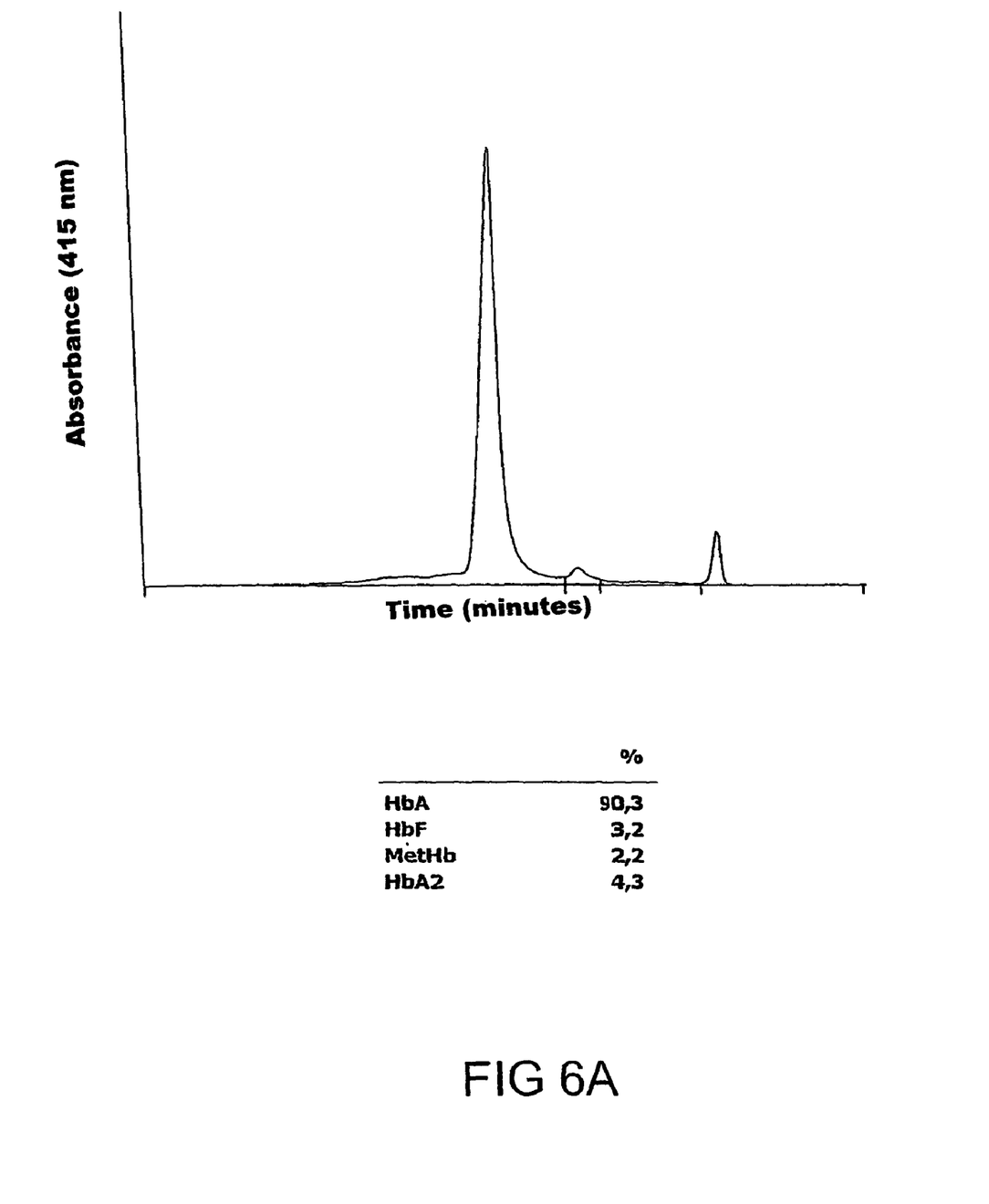
FIGS. 6a, b, c, d each show an electrophoretogram of β-thalassemic blood analyzed by capillary electrophoresis using four different buffer solutions based on four different flow inhibitors.
Figure 6B:
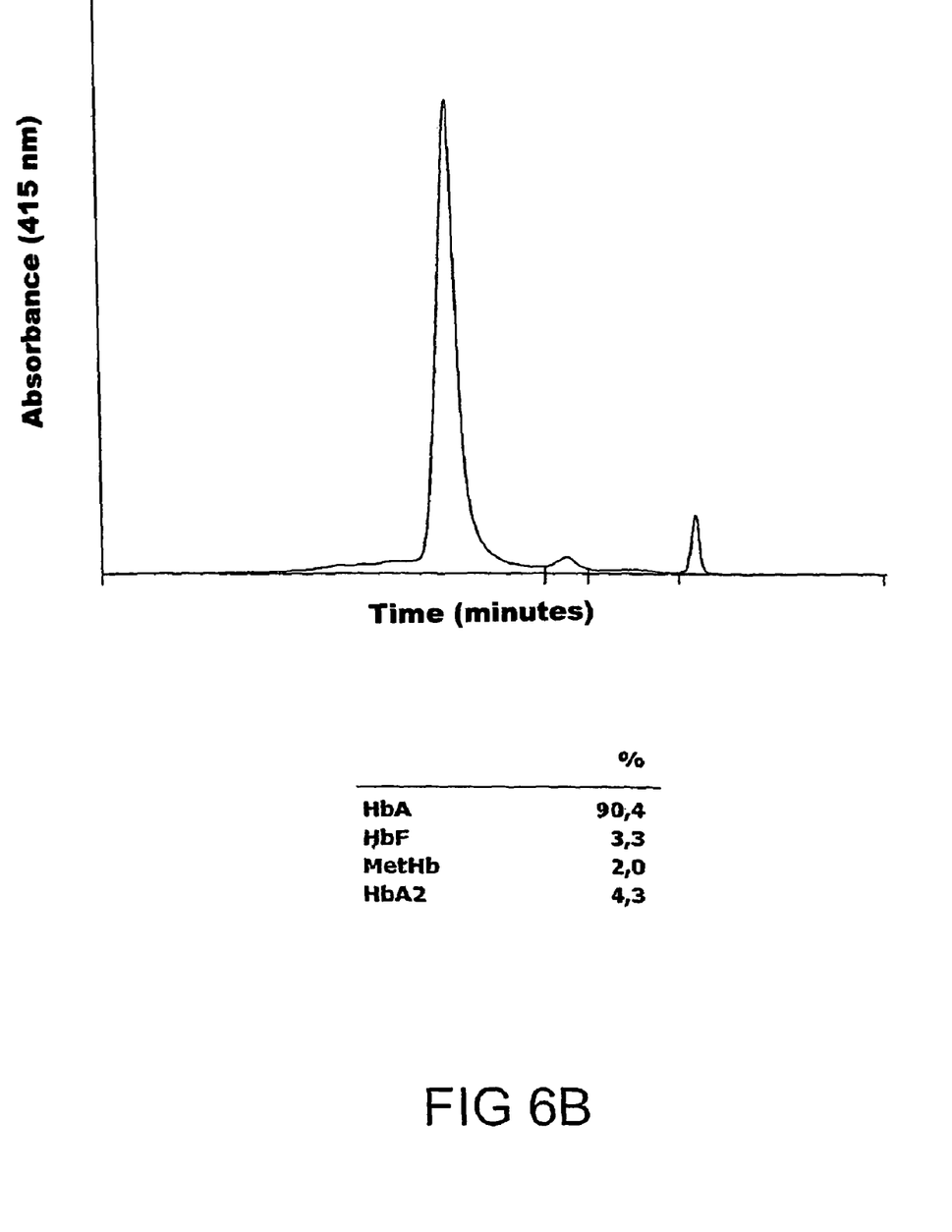
Figure 6C:
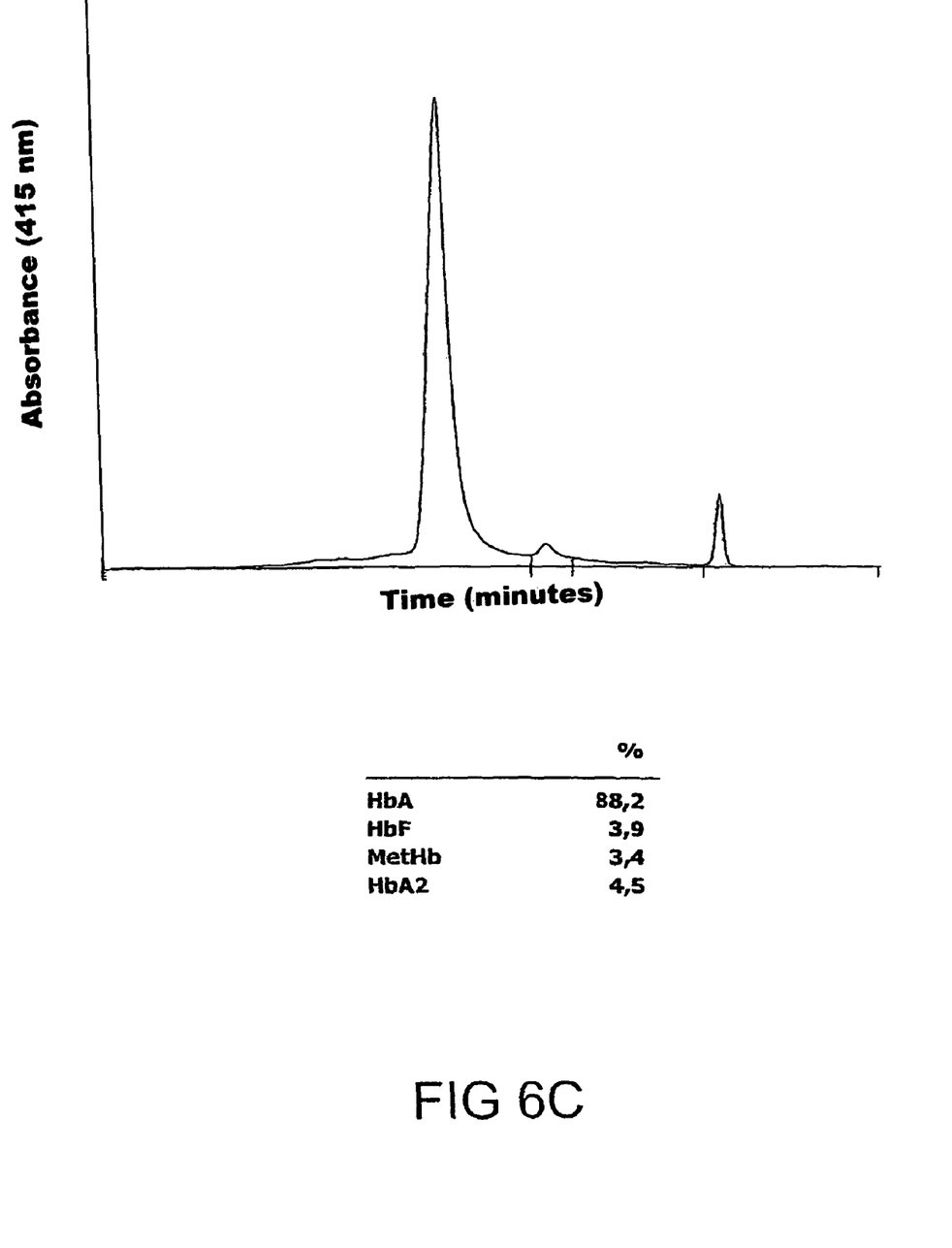
Figure 6D:
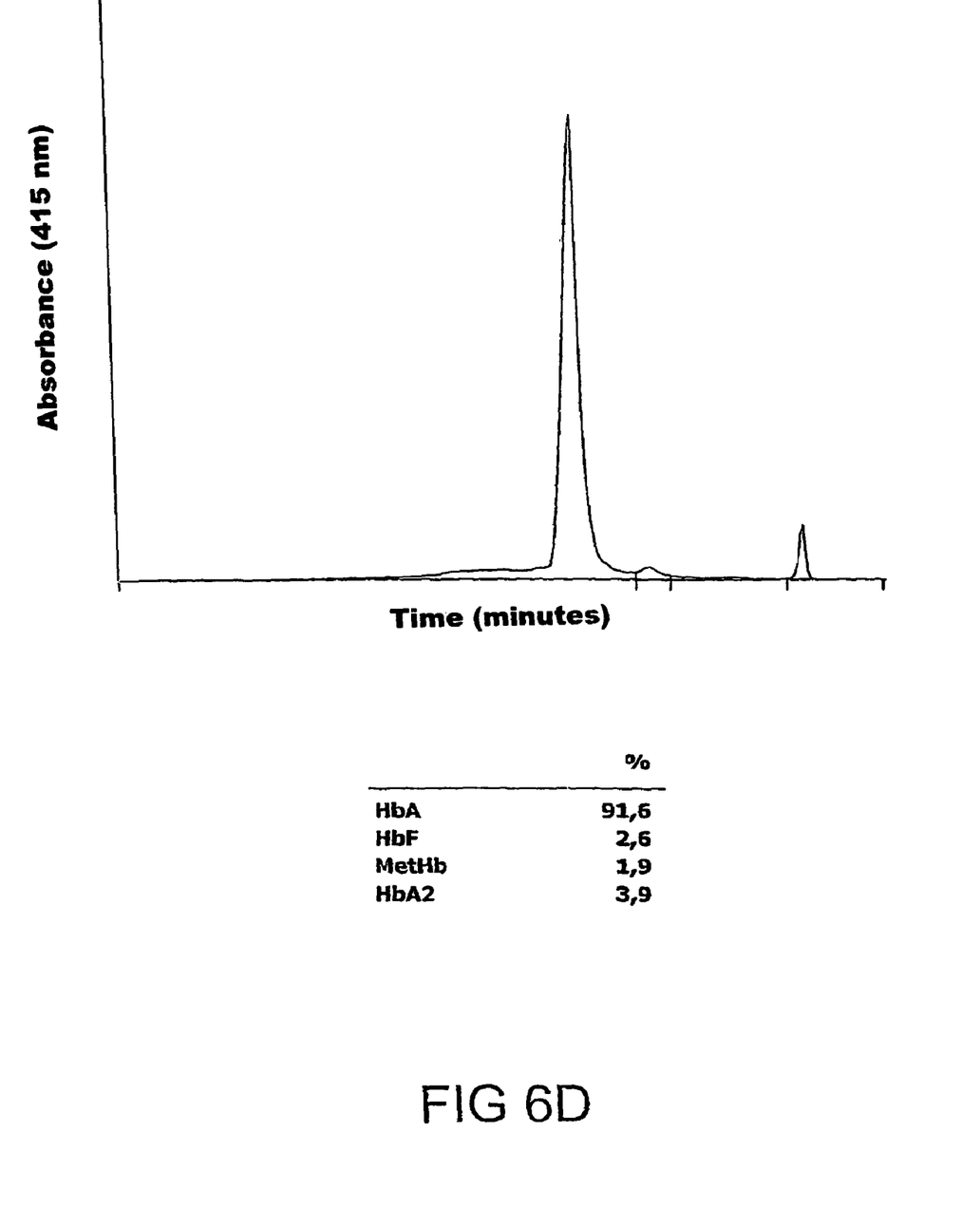
Figure 7A:
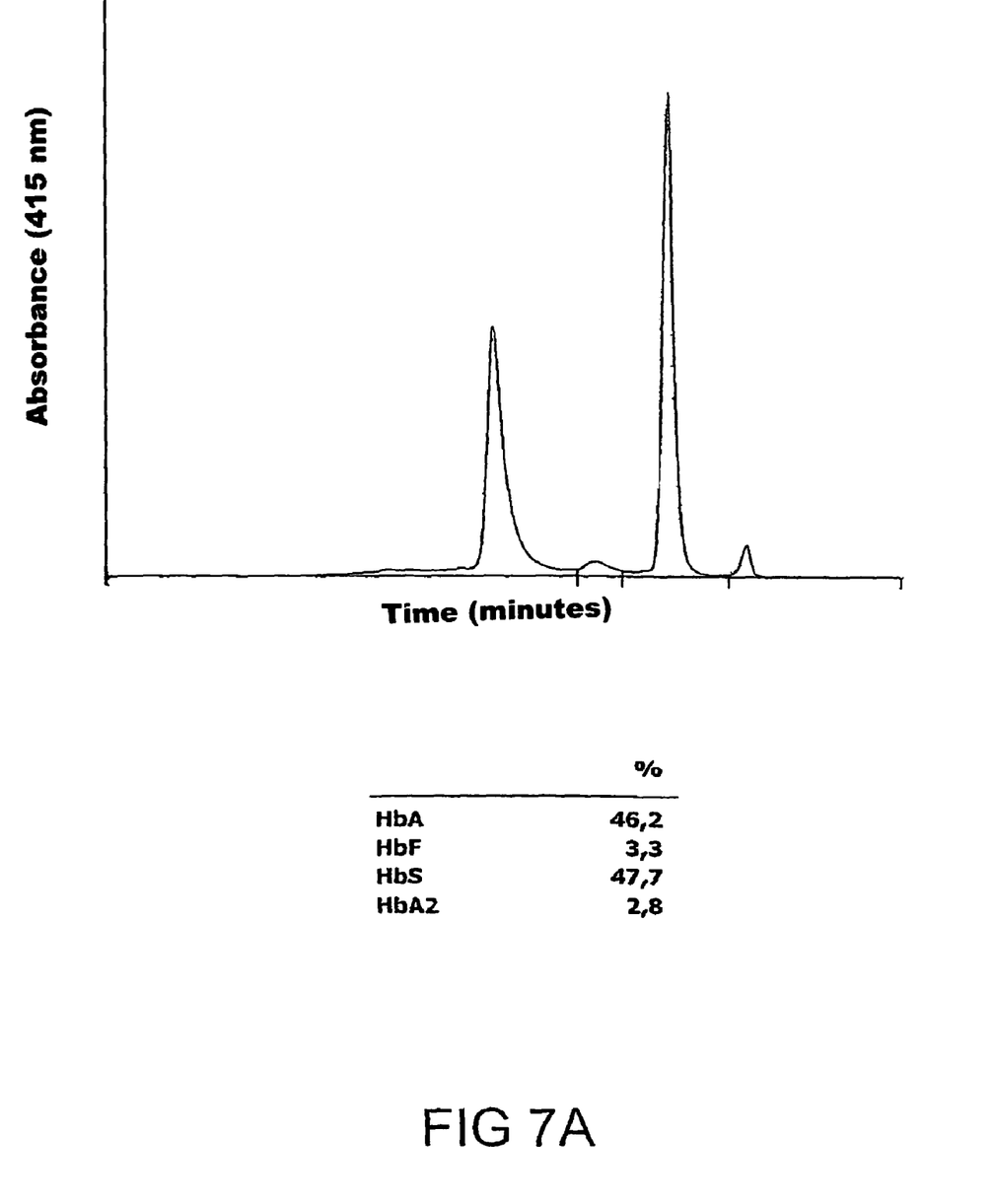
FIGS. 7a, b, c, d each show an electrophoretogram of blood comprising HbF and HbS analyzed by capillary electrophoresis using four different buffer solutions based on four different flow inhibitors.
Figure 7B:
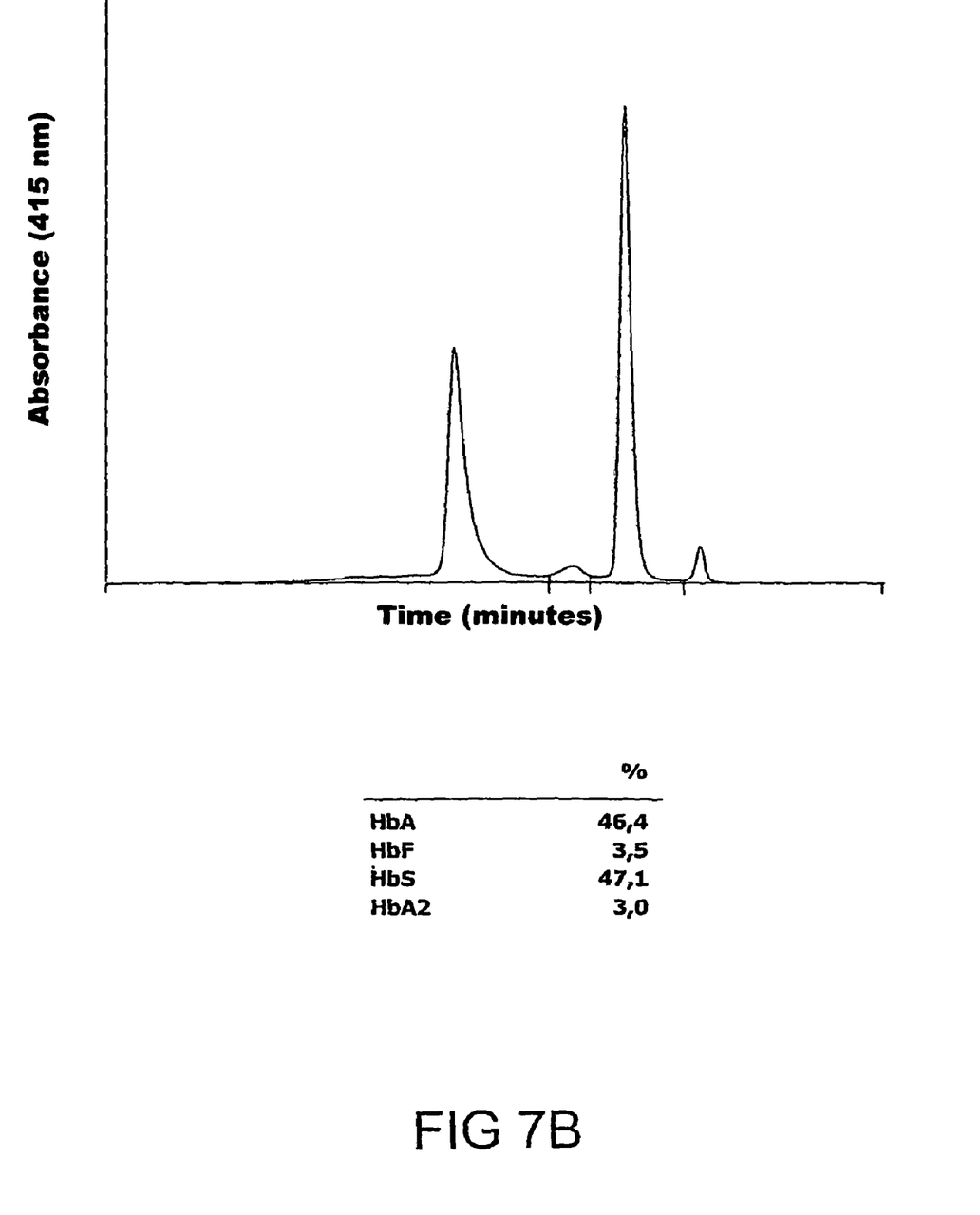
Figure 7C:
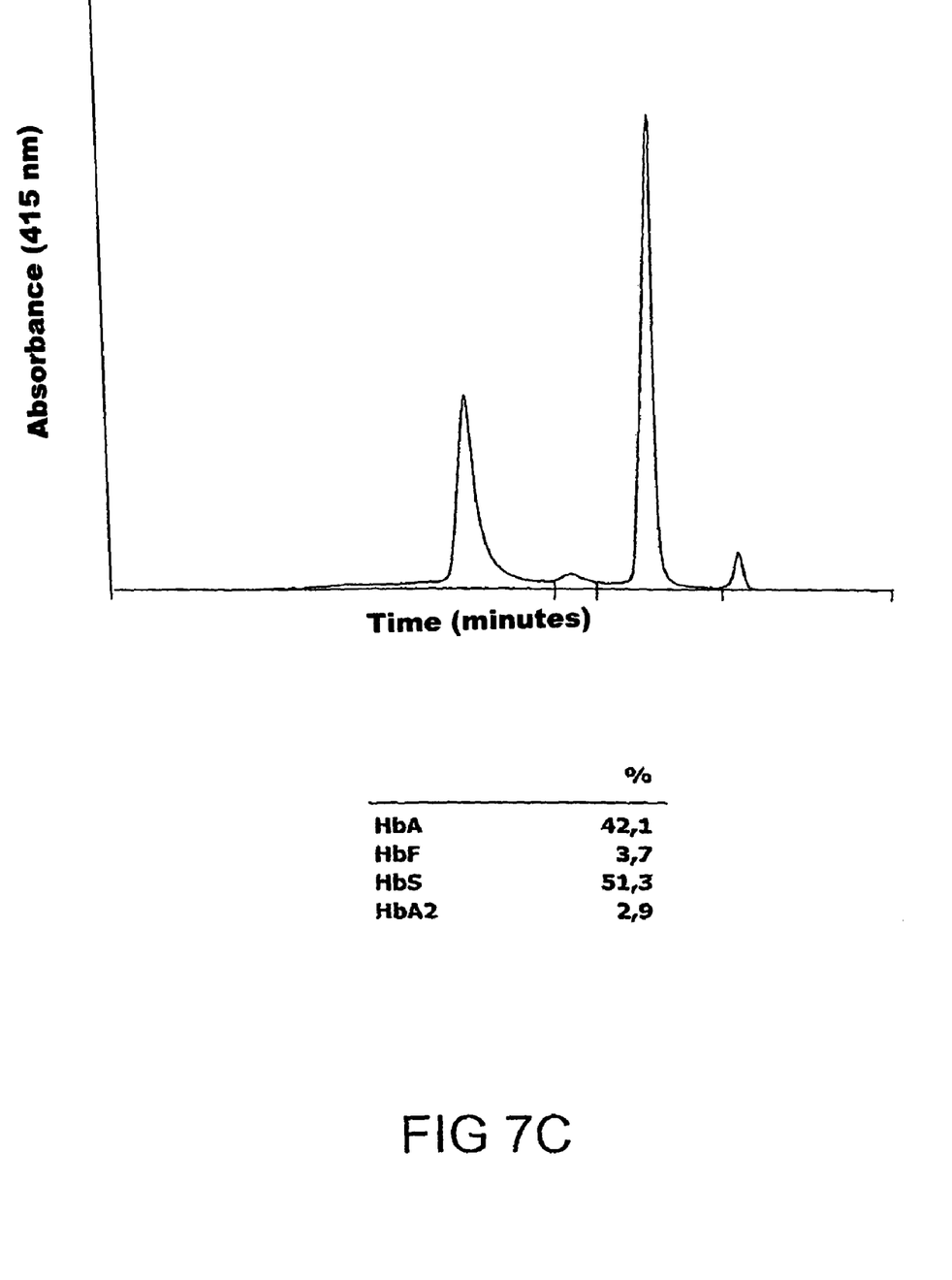
Figure 7D:
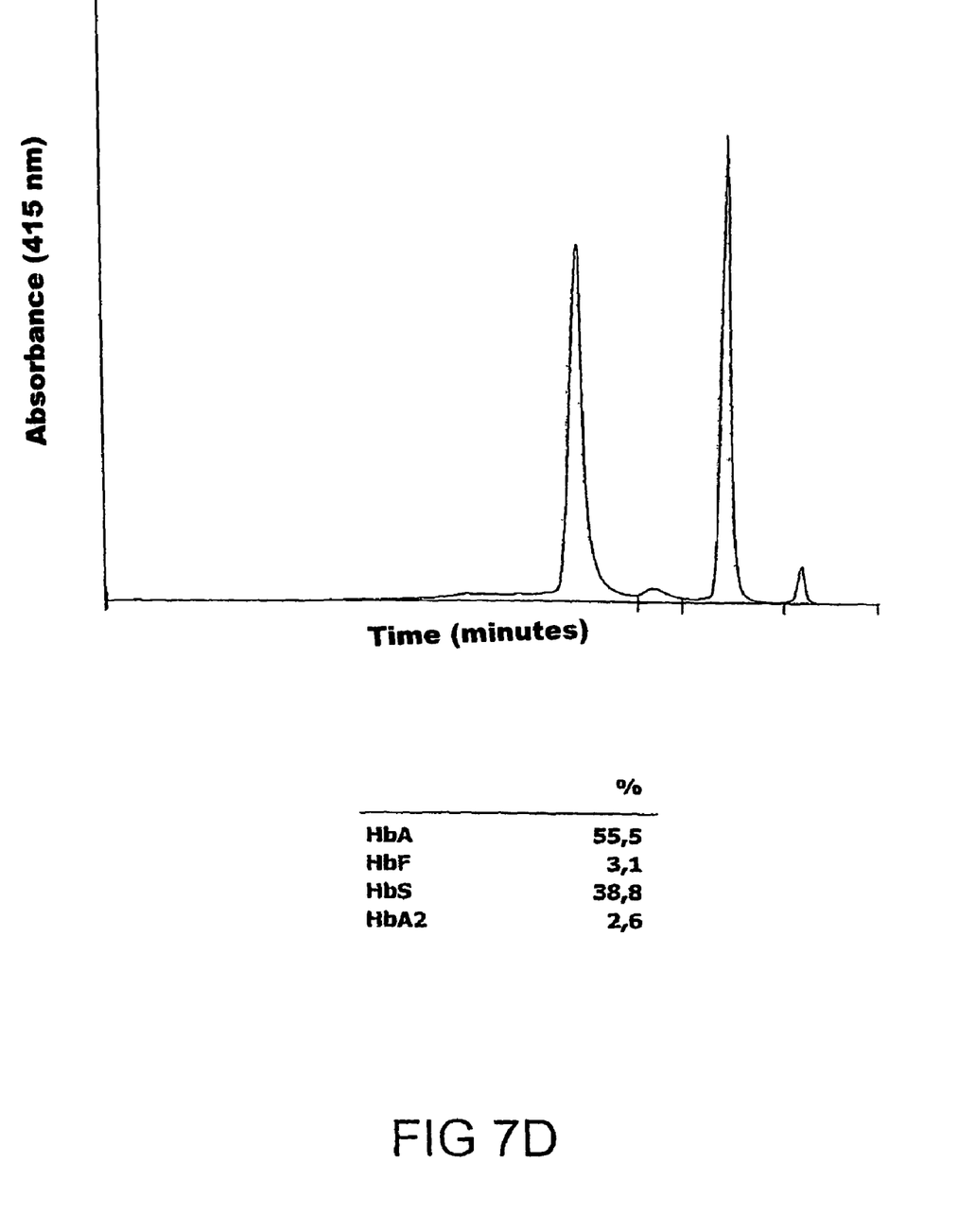

FIG. 6a) shows the results with buffer A (tricine/DAB.2HCl). FIG. 6b shows the results with buffer B (tricine/1,5-diaminopentane.2HCl). FIG. 6c shows the results with buffer C (tricine/DETA). FIG. 6d shows the results with buffer D (tricine/N,N,N',N'-tetramethyl-1,4-butanediamine).

A comparison of these four figures shows that in all cases, separation of each of the fractions was good and the small HbF and $HbA_2$ fractions are well focused.

Example 7: analysis of human blood presenting drepanocytary (sickle cell) heterozygosity (HbS/HbA).

Four analysis buffer solutions (A: tricine/DAB.2HCl; B: tricine/1,5-diaminopentane.2HCl; C: tricine/DETA; D: tricine/N,N,N',N'-tetramethyl-1,4-butanediamine) were prepared as above (FIG. 7).

Electrophoresis was carried out using the method described above.

The order of the figures corresponds to the buffers mentioned above. Here again, comparable profiles were observed regardless of the buffer used.

REFERENCES

1. Noriaki Ishioka et al, Biomedical Chromatography, vol 6, 224-226 (1992).
2. Ahmet Sahin et al, Journal of Chromatography A, 709 (1995) 121-125.
3. Margaret A Jenkins, Michael D Guerin, Journal of Chromatography B, 682 (1996), 23-34.
4. Margaret A Jenkins, Jean Hendy, Ian L Smith, J CAP ELEC. 004: 3 (1997), 137-143.
5. Margaret A Jenkins, Sujiva Ratnaike, Clinica Chimica Acta 289 (1999) 121-132.
6. Zak K Shihabi et al., Electrophoresis, 21 (2000), 749-752.
7. James M Hempe, Randall D Craver, Electrophoresis, 21 (2000) 743-748.

The invention claimed is:

1. A free solution capillary electrophoresis method for separating and resolving haemoglobins in a biological sample by capillary electrophoresis, said biological sample being a blood sample, said method comprising:
   introducing said biological sample into a capillary tube comprising a solution of an analysis buffer, wherein said analysis buffer is of the zwitterionic type and at least one flow inhibitor, and
   electrophoresing said biological sample in said analysis buffer and at least one said flow inhibitor, whereby said haemoglobins are separated by migration, and wherein said haemoglobins are a haemoglobin HbA2 and an HbC, an HbD, an HbE, an HbS, an HbF or an HbA haemoglobin.

2. The method according to claim 1, further comprising detecting said haemoglobins.

3. The method according to claim 1, wherein the zwitterionic buffer is formed by one or two molecules and comprises at least one amine function, at least one acid function and at least one hydroxyl function in the position opposite to the acid function.

4. The method according to claim 1, wherein said at least one flow inhibitor is of an aliphatic or a cyclic diamine or a polyamine type.

5. The method according to claim 1, wherein said at least one flow inhibitor is selected from the group consisting of aliphatic diamines, aliphatic polyamines, their acceptable derivatives and salts, and mixtures thereof.

6. The method according claim 1, wherein said analysis buffer has a concentration in said analysis buffer solution from about 20 mM to about 500 mM.

7. The method according to claim 1, wherein said analysis buffer has a concentration in said analysis buffer solution from about 100 mM to about 250 mM.

8. The method according to claim 1, wherein said at least one flow inhibitor has a concentration from about 0.01 mM to about 50 mM in said analysis buffer solution.

9. The method according to claim 1, wherein said at least one flow inhibitor has a concentration from about 0.10 mM to about 20 mM in said analysis buffer solution.

10. The method according to claim 1, wherein said capillary tube is naked.

11. The method according to claim 1, wherein said capillary tube is formed from fused silica.

12. The method according to claim 1, wherein said analysis buffer solution has a pH from about 8 to about 10.

13. The method according to claim 1, wherein said blood sample is selected from the group consisting of normal blood, abnormal blood, washed blood, decanted blood, centrifuged blood haemolyzed blood, and whole blood.

14. The method according to claim 13, wherein said blood sample is a sample of haemolyzed blood.

15. The method according to claim 1, wherein said analysis buffer is selected from tricine, TAPS, TABS, AMPSO, bicine or HEPBS, or an association of Tris, AMPD or bis Tris propane with an amino acid.

16. The method according to claim 15, wherein said analysis buffer is tricine.

17. The method according to claim 1, wherein said analysis buffer solution further comprises a pH modifier.

18. The method according to claim 17, wherein said pH modifier is selected from the group consisting of lithium hydroxide, sodium hydroxide, potassium, hydroxide, rubidium hydroxide, caesium hydroxide, francium hydroxide, mono-alkylammonium hydroxide, di-alkylammonium hydroxide, tri-alkylammonium hydroxide and tetra-alkylammonium hydroxide said alkylammonium hydroxide containing 1 to 8 carbon atoms in the alkyl portion.

19. The method according to claim 1, wherein said an least one flow inhibitor is selected from the group consisting of 1,3-diaminopropane, 1,4-diaminobutane, 1,5-diaminopentane, 1,6-diaminohexane, diethylenetriamine, spermine, N,N'-dimethyl-1,6-hexanediamine, tetraethylenepentamine, N,N,N',N'-tetramethyl-1,4-butanediamine, their acceptable derivatives and salts, and mixtures thereof.

20. The method according to claim 19, wherein said at least one flow inhibitor is selected from the group consisting of 1,4-diaminobutane, 1,5-diaminopentane, 1,6-diaminohexane, diethylenetriamine and N,N,N',N'-tetramethyl-1,4-butanediamine, their acceptable derivatives and salts, and mixtures thereof.

21. The method according to claim 20, wherein said at least one flow inhibitor is 1,4-diaminobutane.

22. The method according to claim 21, wherein said at least one flow inhibitor is 1,4-diaminobutane in the hydrochloride form.

23. A free solution capillary electrophoresis method for separating and resolving haemoglobins in a biological sample by capillary electrophoresis, said biological sample being a blood sample, said sample being selected from the group consisting of normal blood, abnormal blood, washed blood, decanted blood, centrifuged blood, whole blood and haemolyzed blood, said method comprising:
   introducing said biological sample into a capillary tube comprising a solution of an analysis buffer, wherein said analysis buffer is of the zwitterionic type and at least one flow inhibitor, and
   electrophoresing said biological sample in said analysis buffer and at least one said flow inhibitor, whereby said haemoglobins are separated by migration.

24. A free solution capillary electrophoresis method for separating and resolving haemoglobins in a biological sample by capillary electrophoresis, said biological sample being a blood sample, said method comprising:
   introducing said biological sample into a capillary tube comprising a solution of an analysis buffer, wherein said analysis buffer is of the zwittenionic type and at least one flow inhibitor, said flow inhibitor being an aliphatic or a cyclic diamine or a polyamine type, and
   electrophoresing said biological sample in said analysis buffer and at least one said flow inhibitor, whereby said haemoglobins are separated by migration.

* * * * *